United States Patent [19]

Hornby et al.

[11] 4,376,165

[45] Mar. 8, 1983

[54] METHOD OF PREPARING AN ENZYME-LABELED LIGAND FOR USE IN SPECIFIC BINDING ASSAYS AND THE LABELED CONJUGATE PRODUCED THEREBY

[75] Inventors: William E. Hornby, Berkshire; David L. Morris, Buckinghamshire, both of England

[73] Assignee: Miles Laboratories, Inc., Elkhart, Ind.

[21] Appl. No.: 244,047

[22] Filed: Mar. 16, 1981

Related U.S. Application Data

[63] Continuation of Ser. No. 917,961, Jun. 22, 1978, abandoned.

[51] Int. Cl.$^3$ .................. C12N 9/96; G01N 33/54; C12N 9/04; C12N 9/02
[52] U.S. Cl. .................................. 435/188; 435/7; 435/189; 435/190
[58] Field of Search ............... 435/7, 177, 188, 810, 435/189, 190; 260/112 R, 121; 536/4, 23, 24; 23/230 B; 424/8, 12

[56] References Cited

U.S. PATENT DOCUMENTS

| | | | |
|---|---|---|---|
| 3,879,262 | 4/1975 | Schunrs et al. | 435/7 |
| 3,935,074 | 1/1976 | Rubenstein et al. | 435/7 |
| 3,998,943 | 12/1976 | Ullman | 435/7 |
| 4,040,907 | 8/1977 | Ullman et al. | 435/7 |
| 4,134,792 | 1/1979 | Boguslaski et al. | 424/12 |
| 4,171,432 | 10/1979 | Currico | 435/7 |
| 4,230,797 | 10/1980 | Boguslaski et al. | 435/7 |
| 4,238,565 | 12/1980 | Hornby et al. | 435/7 |

*Primary Examiner*—Thomas G. Wiseman
*Attorney, Agent, or Firm*—Andrew L. Klawitter

[57] ABSTRACT

A method of preparing an enzyme-labeled ligand for use in specific binding assays for determining said ligand or a specific binding partner thereof, by covalently coupling said ligand or a binding analog thereof to an organic prosthetic group and combining the resulting coupled product with an apoenzyme to form a conjugated enzyme complex with said prosthetic group in said coupled product. Preferably, the conjugated enzyme complex in the resulting labeled conjugate exhibits holoenzyme activity which is affected by binding of said labeled conjugate by a specific binding partner of said ligand. Preferred prosthetic groups are flavin mononucleotide, heme, and, especially, flavin adenine dinucleotide, with preferred apoenzymes being apoperoxidase and, especially, apoglucose oxidase.

21 Claims, No Drawings

METHOD OF PREPARING AN ENZYME-LABELED LIGAND FOR USE IN SPECIFIC BINDING ASSAYS AND THE LABELED CONJUGATE PRODUCED THEREBY

This is a continuation of application Ser. No. 917,961, filed June 22, 1978, abandoned.

BACKGROUND OF THE INVENTION

1. Field of the Invention

This invention relates to assay methods, and reagent means for use therein, of the homogeneous or heterogeneous specific binding type for determining qualitatively or quantitatively a ligand in a liquid medium. In particular, the invention relates to specific binding assays employing non-radioisotopic labels. Further, the invention relates to non-radioisotopic labeled conjugates for use in such assays and to methods of their preparation.

2. Description of the Prior Art

In conventional specific binding assay techniques, the test sample is combined with reagent means of various compositions that include a conjugate having a monitorable label component and a binding component which participates with other constituents, if any, of the reagent means to form a binding reaction system producing two species or forms of the labeled conjugate, a bound-species and a free-species. The relative amount or proportion of the labeled conjugate that results in the bound-species compared to the free-species is a function of the presence (or amount) of the ligand to be detected in the test sample.

As an illustration a conventional competitive binding assay technique will now be described. In such a technique the reagent means would comprise (1) a labeled conjugate in the form of the ligand to be detected (e.g., an antigen or hapten), such ligand constituting the binding component of the conjugate, chemically linked to a label component, and (2) a specific binding partner for the ligand (e.g., an antibody). Upon combination of the test sample and the reagent means, the ligand to be detected and the binding component of the labeled conjugate would compete in a substantially nondiscriminating manner for noncovalent binding to the specific binding partner. As a result, either the amount of labeled conjugate that would become bound to the binding partner (i.e., that results in the bound-species) or that amount which would remain free (i.e., unbound to the binding partner and thus that results in the free-species) can be measured as a function of the amount of competing ligand present. The amount of labeled conjugate resulting in either species is determined by measuring, i.e., monitoring, the label component therein.

Where the labeled conjugate in the bound-species and that in the free-species are essentially indistinguishable by the means used to monitor the label component, the bound-species and the free-species must be physically separated in order to complete the assay. This type of assay is referred to in the art as "heterogeneous". Where the bound-species and free-species forms of the labeled conjugate can be distinguished, a "homogeneous" format may be followed and the separation step avoided.

The first discovered type of highly sensitive specific binding assay was the radioimmunoassay which employs a radioactive isotope as the label component. Such an assay necessarily must follow the heterogeneous format since the monitorable character of the label is qualitatively unchanged in the free- and bound-species. Because of the inconvenience and difficulty of handling radioactive materials, many new assay systems have been devised using materials other than radioisotopes as the label component, including enzymes, fluorescent molecules, bacteriophages, metals and organometallic complexes, coenzymes, enzyme substrates, enzyme inhibitors, cyclic reactants, and chemiluminescent reactants.

The following describe several different heterogeneous binding reaction systems in which an enzyme is employed as the label component: U.S. Pat. Nos. 3,654,090; 3,791,932; 3,839,153; 3,850,752; and 3,879,262; *J. Immunol. Methods* 1:247 (1972); and *J. Immunol.* 109:129(1972). A heterogeneous binding assay utilizing a non-active precursor of a spectrophotometrically detectable substance as the labeling substance is suggested in U.S. Pat. No. 3,880,934. Of further background interest pertaining to heterogeneous assays is *Principles of Competitive Protein-Binding Assays*, ed. Odell and Daughaday (J. B. Lippincott Co., Philadephia, 1972).

An enzyme-labeled immunoassay of the homogeneous type is described in U.S. Pat. No. 3,817,834 wherein a ligand-enzyme conjugate is employed. The enzymatic activity of the conjugate in the bound-species is measurably less than that in the free-species, thereby allowing a homogeneous format to be used. The use of particularly unique materials as labeling substances, including coenzymes, chemiluminescent molecules, cyclic reactants, and cleavable fluorescent enzyme substrates, in both homogeneous and heterogeneous formats, is described in German Offenlegungschriften Nos. 2,618,419 and 2,618,511 based on U.S. patent applications Ser. Nos. 667,982 and 667,996, filed on Mar. 18, 1976, and assigned to the present assignee.

While the search for non-radioisotopic labels in binding assays has produced a number of workable solutions, there remains room for improvement. The enzyme-labeled approaches appeared at first to be the most promising, however, in practice several difficulties have come to light. The high molecular weight and heterologous nature of enzymes creates problems in characterizing, stabilizing, and reproducibly preparing the labeled conjugates. These problems were overcome by replacing enzyme-labels with low molecular weight labels monitorable by their reactant activity. These novel labels, including coenzymes, enzyme substrates, cyclic reactants and chemiluminescent reactants, can be used to form assays of high sensitivity and versatility. However, monitoring of these labels often requires instrumentation which for the present is not commonly found in the clinical laboratory.

It is a primary object of the present invention to provide a non-radioisotopic binding assay employing a novel label which is monitorable with standard clinical laboratory equipment while retaining the reactant-label advantages of sensitivity, versatility, and ease of synthesis and characterization of labeled conjugates.

SUMMARY OF THE INVENTION

It has now been found that an improved specific binding assay is provided by employing an organic prosthetic group residue as a label component in the labeled conjugate. Prosthetic groups are an art recognized class of enzyme cofactors. An enzyme cofactor is a nonprotein substance whose presence is required for an enzyme to exhibit its catalytic activity and which undergoes a chemical change during the catalytic cycle of the enzyme involves (referred to as the parent enzyme). A coenzyme is a type of enzyme cofactor which is chemically modified in the course of the reaction catalyzed by the parent enzyme. Regeneration of the original form of the cofactor requires its participation in a separate reaction that is catalyzed by an enzyme other than the parent enzyme. In contrast, a prosthetic group is an enzyme cofactor which is chemically modified in the course of the reaction catalyzed by the parent enzyme and is regenerated, i.e., reconverted to its original form, by a second reaction catalyzed by the same parent enzyme.

Prosthetic groups are usually characterized by being firmly bound in relative terms to the protein portion of the parent enzyme, such protein portion being known as the apoenzyme and the catalytically active parent enzyme being known as the holoenzyme. The equilibrium reaction for the interaction between a prosthetic group and apoenzyme may be represented as follows:

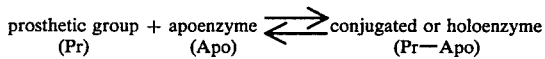

prosthetic group + apoenzyme ⇌ conjugated or holoenzyme
(Pr)           (Apo)              (Pr—Apo)

As used herein, the term conjugated enzyme refers to the complex formed by combination of the prosthetic group and apoenzyme whether or not such complex exhibits catalytic activity, and the term holoenzyme refers only to a catalytically active conjugated enzyme. Further information concerning prosthetic groups, their characteristics, and their interactions with apoenzymes may be obtained by referring to Dixon and Webb, *Enzymes*, 1st ed., Longmans, Green and Co. (London 1958).

In the present invention an organic prosthetic group is coupled to a binding component to form a labeled conjugate for use in binding assays. A central feature of the invention is the resulting interaction between the conjugated prosthetic group and apoenzyme illustrated as follows:

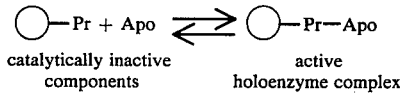

○—Pr + Apo ⇌ ○—Pr—Apo
catalytically inactive      active
components              holoenzyme complex While the above-represented reaction is the normally observed interaction it is anticipated that in certain circumstances the conjugated enzyme complex will exhibit little or no holoenzyme activity, such as where conjugation of the prosthetic group prevents normal holoenzyme-substrate interaction. Labeled conjugates of use in the present invention may nonetheless result if, upon binding of the binding component (represented by the symbol ○– above) of the conjugated prosthetic group in the assay binding reaction, the bound conjugated enzyme complex then does exhibit holoenzyme activity, such as where such binding relieves the inhibition of holoenzyme-substrate interaction.

There are numerous possible label monitoring schemes, some of which are illustrated hereinafter, following any of the various known homogeneous and heterogeneous binding formats. However, in all cases the label component of the labeled conjugate that participates in the binding reaction comprises an organic prosthetic group residue and the monitoring scheme comprises determining the label component in the bound-species or the free-species, or both, as the case may be, based on measurement of holoenzyme activity.

Prosthetic group residues which are preferably used in the present invention are residues of flavin adenine dinucleotide, flavin mononucleotide, and heme. Preferable prosthetic group residue/apoenzyme pairs are residues of flavin adenine dinucleotide/apoglucose oxidase and residues of heme/apoperoxidase. The respective holoenzymes formed from such pairs are readily monitored with the well-known hydrogen peroxide measurement techniques which include colorimetric and fluorometric methods. Due to the catalytic nature of the monitored holoenzyme, the presence of the label component is amplified manyfold in the monitoring reaction, permitting highly sensitive detection of the ligand under assay (e.g., at levels of ng/ml) using relatively insensitive but readily available and simple instrumentation, such as spectrophotometers. The combination of the ability to use a low molecular weight prosthetic group molecule as the component through which the label is coupled to the binding component in the labeled conjugate and the ability to attain highly sensitive detection with spectrophotometric, particularly colorimetric, read-out provides a uniquely advantageous specific binding assay.

The present assay is characterized by highly sensitive detection limits, by being readily adaptable to automation, by permitting the label to be monitored with instrumentation commonly found in clinical laboratories, and by utilizing labeled conjugates that can be reproducibly and relatively simply synthesized.

DESCRIPTION OF THE PREFERRED EMBODIMENTS

In the context of this disclosure, the following terms shall be defined as follows unless otherwise indicated: "ligand" is the substance, or class of related substances, whose presence or the amount thereof in a liquid medium is to be determined; "specific binding partner of the ligand" is any substance, or class of substances, which has a specific binding affinity for the ligand to the exclusion of other substances; "specific binding analog of the ligand" is any substance, or class of substances, which behaves essentially the same as the ligand with respect to the binding affinity of the specific binding partner for the ligand; "residue" is a moiety in an organic molecule, for example, a prosthetic group residue in a labeled conjugate is an organic moiety in such conjugated derived from and functioning essentially as a prosthetic group, such as the prosthetic group less a hydrogen atom at a position through which the prosthetic group is coupled to the remaining portion of the labeled conjugate (in an FAD-ligand labeled conjugate, FAD represents a residue of the prosthetic group flavin adenine dinucleotide); "reagent means" is a composition, device or test kit comprising the reagents used to perform an assay method; "monitoring reaction" is the reaction in which the label conponent of the labeled conjugate is determined by measuring holoenzyme activity; "lower alkyl" is a straight chain or branched alkyl group comprising from 1 to 6 carbon atoms, inclusive, such as methyl, ethyl, isopropyl, and hexyl.

The present assay may be applied to the detection of any ligand for which there is a specific binding partner. The ligand usually is a peptide, protein, carbohydrate, glycoprotein, steroid, or other organic molecule for which a specific binding partner exists in biological systems or can be synthesized. The ligand, in functional terms, is usually selected from the group consisting of antigens and antibodies thereto; haptens and antibodies thereof; and hormones, vitamins, metabolites and pharmacological agents, and their receptors and binding substances. Specific examples of ligands which may be detected using the present invention are hormones such as insulin, chorionic gonadotropin, thyroid hormones, and estriol; antigens and haptens such as ferritin, bradykinin, prostaglandins, and tumor specific antigens; vitamins such as biotin, vitamin $B_{12}$, folic acid, vitamin E, vitamin A, and ascorbic acid; metabolites such as 3',5'-adenosine monophosphate and 3',5'-guanosine monophosphate; pharmacological agents or drugs, such as anti-convulsants, bronchodialators, cardiovascular agents, and drugs of abuse; antibodies such as microsomal antibody and antibodies to hepatitis and allergens; and specific binding receptors such as thyroxine binding globulin, avidin, intrinsic factor, and transcobalamin. The present assay is particularly useful for the detection of haptens, and analogs thereof, of molecular weight between 100 and 1000, particularly the iodothyronine thyroid hormones thyroxine and liothyronine.

The liquid medium to be tested may be a naturally occurring or artificially formed liquid suspected of containing the ligand, and usually is a biological fluid or a liquid resulting from a dilution or other treatment thereof. Biological fluids which may be assayed following the present method include serum, plasma, urine, saliva, and amniotic and cerebrospinal fluids. Other materials such as solid matter, for example tissue, may be assayed by reducing them to a liquid form, such as by dissolution of the solid in a liquid or by liquid extraction of the solid.

LABELED CONJUGATE

The labeled conjugate of the present invention comprises an organic prosthetic group residue in its label component and may be in either of two basic forms schematically represented as follows:

| schematic formula | label component |
|---|---|
| Pr—R—L | prosthetic group residue (Pr—) |
| Apo—Pr—R—L | holoenzyme or conjugated enzyme residue (Apo—Pr—) | wherein Pr represents the prosthetic group residue and Apo the apoenzyme, R is a linking group, and L is the binding component of the labeled conjugate, usually the ligand or a binding analog thereof. Usually, the binding component and the prosthetic group residue are coupled through the linking group at a site on the former away from its specific binding locus (i.e., the location on the binding component which participates in the assay binding reaction, such as an immunochemical binding site where the binding component is an antigen, hapten or antibody thereto) and at a site on the latter away from its active binding site for the apoenzyme.

ASSAY METHODS

There are various methods available for monitoring the novel labeled conjugates according to the present invention. In every case the prosthetic group residue is covalently coupled to the binding component in the labeled component and the monitoring reaction comprises measuring holoenzyme activity in the bound-species or free-species, or both, as the case may be.

For purposes of illustration only, the following are examples of several monitoring schemes based on homogeneous and heterogeneous competitive binding techniques whereas it will be understood that other homogeneous and heterogeneous techniques can be followed in practice.

In the illustrations below, the following abbreviations will be used consistent with the remaining description herein:

| term | abbreviation |
|---|---|
| prosthetic group residue | Pr |
| apoenzyme | Apo |
| linking group | R |
| ligand | L |
| binding partner | B |
| conjugated enzyme residue | Apo—Pr |
| holoenzyme residue (active) | Apo—Pr |

ILLUSTRATIVE MONITORING SCHEME #1

Homogeneous Competitive Binding Method—Apoenzyme Introduced After Initiation of Binding Reaction

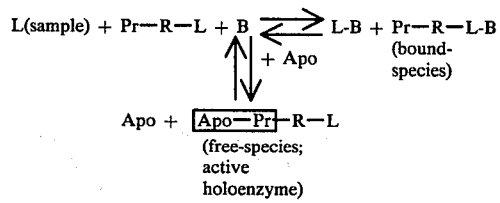

In this scheme, the prosthetic group residue as label component is monitored by adding apoenzyme substantially simultaneous with or after initiation of the binding reaction, i.e., during the binding reaction or after the binding reaction has reached equilibrium, and measuring the holoenzyme activity in the final reaction mixture. The assay is homogeneous by selection of conditions such that binding of apoenzyme with the prosthetic group residue is inhibited for the prosthetic group in the bound-species. Or conditions might be selected such that apoenzyme can bind to the bound-species form of the labeled conjugate but the resulting conjugated enzyme complex exhibits no enzymatic activity such as because of inhibition of enzyme-substrate interaction (this situation is not shown in the above schematic). In either case, the total amount of enzyme activity measured in the system is the result of uninhibited binding of apoenzyme to free labeled conjugate and accordingly is a direct function of the amount of ligand from the sample available for competition for binding to the binding partner.

It might also occur (but also is not shown above) that, in contrast to the above schemes, the labeled conjugate (Pr-R-L) is formed such that binding with the apoenzyme is inhibited but that upon binding of the labeled conjugate by the binding partner such inhibition is relieved and apoenzyme is able to bind with the bound-species form of the labeled conjugate to form an active holoenzyme complex. In such a case, the amount of holoenzyme activity resulting in the system is an inverse function of the amount of ligand present in the sample.

ILLUSTRATIVE MONITORING SCHEME #2

Heterogeneous Competitive Binding
Method—Apoenzyme Introduced After Initiation of
Binding Reaction

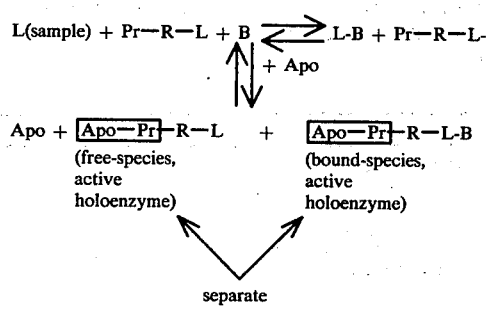

This scheme involves the same reagents and order of addition as above-described scheme #1 except that conditions are such that apoenzyme can bind to the labeled conjugate in the bound-species to form an active holoenzyme complex qualitatively indistinguishable from that formed by binding to the free-species form of the labeled conjugate. The bound-species and free-species must be separated and the enzyme activity in one thereof is a function of the amount of ligand present in the sample.

ILLUSTRATIVE MONITORING SCHEME #3

Homogeneous Competitive Binding
Method—Apoenzyme Introduced Prior to Initiation of
Binding Reaction

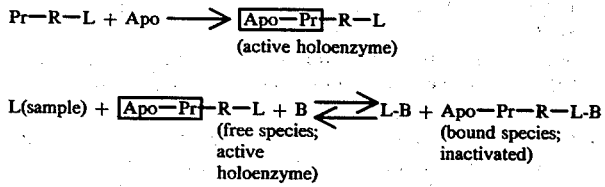

In this scheme, the prosthetic group residue is comprised in the label component by being coupled to the ligand and combined with the apoenzyme in the form of an active holoenzyme product. The prosthetic group residue is monitored by measuring holoenzyme activity in the final reaction mixture. The assay is homogeneous by selection of conditions such that upon binding of the binding partner to the active holoenzyme complex the bound-species form that results exhibits inhibited enzyme activity such as because of inhibition of enzyme-substrate interaction. The total amount of enzyme activity measured in the system is the result of unbound active holoenzyme complex, i.e., the free-species form, and accordingly is a duct function of the amount of ligand present in the sample.

It might also occur (but is not shown above) that, in contrast to the above scheme, the labeled conjugate exhibits little or no enzymatic activity but upon binding of the binding partner the bound-species form actually exhibits measurable or enhanced enzymatic activity. In such a case, the amount of holoenzyme activity resulting in the system is an inverse function of the amount of ligand present in the sample.

ILLUSTRATIVE MONITORING SCHEME #4

Heterogeneous Competitive Binding
Method—Apoenzyme Introduced Prior to Initiation of
Binding Reaction

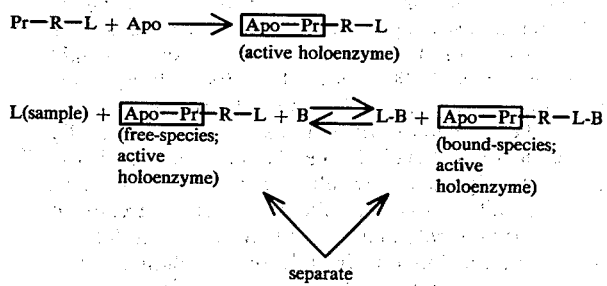

This scheme involves the same reagents and order of addition as above-described scheme #3 except that conditions are such that both the bound-species and free-species forms are enzymatically active and are qualitatively indistinguishable. The bound-species and the free-species must be separated and the enzyme activity in one thereof is a function of the amount of ligand present in the sample.

Schemes #3 and #4 are essentially enzyme-labeled assays except that, in contrast to the prior art, the enzyme as such is coupled to the binding component of the labeled conjugate through a prosthetic group residue. In this respect then, the present invention provides a novel method of preparing an enzyme-labeled conjugate comprising the steps of (a) covalently coupling the binding component moiety (i.e., the ligand to be detected or a binding analog or partner thereof) to an organic prosthetic group which is capable of combining with an apoenzyme to produce a conjugated enzyme, e.g., an active holoenzyme, (b) combining the resulting prosthetic group labeled conjugate with the apoenzyme, and (c) isolating the resulting conjugated enzyme-labeled conjugate. It is contemplated that such a method is most valuable in preparing enzyme-labeled conjugates for use in assays because of the controlled manner in which the low molecular weight and well characterized prosthetic group can be coupled to the binding component.

It is evident from the above discussion that for certain labeled conjugates and ligand/binding partner pairs one or more of the described homogeneous schemes will be appropriate depending upon several factors, including the ability of apoenzyme to bind to the bound-species form of the labeled conjugate and the effect of binding partner binding on the conjugated enzyme complex. Where the bound-species and free-species forms of the labeled conjugate exhibit indistinguishable activity, a heterogeneous format can be followed to provide a useful assay. Accordingly, while circumstances may dictate what particular manipulative scheme or schemes will be most useful, the present assay method, in general, is adaptable to any conventional homogeneous or heterogeneous technique.

HOMOGENEOUS TECHNIQUES

A homogeneous technique, i.e., one which does not require a physical separation of the bound-species and the free-species, is available where reaction between the binding component of the labeled conjugate and a corresponding binding partner causes a measurable change, either in a positive or a negative sense, in the ability of the label component of the labeled conjugate to participate in the monitoring reaction, e.g., in the ability of the labeled conjugate to combine with apoenzyme and/or exhibit holoenzyme activity. In such a case, the distribution of the label component between the bound-species and the free-species can be determined without separation of the species. The holoenzyme activity in the reaction mixture is then determined by forming in at least a portion thereof the chemical reaction catalyzed by such holoenzyme, e.g., by addition of substrate, and measuring by any conventional technique the rate or aggregate amount of product production or reactant consumption. Qualitative determination of the ligand in the liquid medium involves comparing the measured quantity to that of the monitoring reaction in a liquid medium devoid of the ligand, any difference therebetween being an indication of the presence of such ligand in the liquid tested. Quantitative determination of the ligand in the liquid medium involves comparing the measured quantity to that of the monitoring reaction in liquid media containing various known amounts of the ligand, e.g., a comparison to a standard curve.

In general, when following a homogeneous assay technique, the components of the specific binding reaction, i.e., the liquid medium suspected of containing the ligand, the labeled conjugate, and, in some systems (i.e., a competitive binding system), a specific binding partner of the ligand, may be combined in any amount, manner, and sequence, provided that the activity of the label component of the labeled conjugate is measurably altered when the liquid medium contains the ligand in an amount or concentration of significance to the purposes of the assay. Preferably, all of the components of the specific binding reaction are soluble in the liquid medium.

Known variations of the above briefly described homogeneous methods and further details concerning the specific techniques discussed, including an alternative technique known as the direct binding technique, are readily available in the literature, e.g., German OLS No. 2,618,511, corresponding to U.S. patent application Ser. No. 667,996, filed Mar. 18, 1976 and assigned to the present assignee.

HETEROGENEOUS TECHNIQUES

The use of the present novel labels can also be applied to the conventional heterogeneous type assay techniques wherein the bound- and free-species of the labeled conjugate are separated and the label component in one or the other is determined. The reagent means for performing such a heterogeneous assay may take many different forms. In general, such means comprises three basic constituents, which are (1) the ligand to be detected, (2) a specific binding partner of the ligand, and (3) the labeled conjugate. The binding reaction constituents are combined simultaneously or in a series of additions, and with an appropriate incubation period or periods, the labeled conjugate becomes bound to its corresponding binding partners such that the extent of binding, i.e., the ratio of the amount of labeled conjugate bound to a binding partner (the bound-species) to that unbound (the free-species), is a function of the amount of ligand present. The bound- and free-species are physically separated and the amount of label present in one thereof is determined by measuring the holoenzyme activity therein and comparing such to a negative control or standard results, e.g., a standard curve.

Various means of performing the separation step and of forming the binding reaction systems are available in the art. Separation may involve such conventional techniques as those involving what is commonly known as a solid-phase antibody or antigen, a second antibody, or a solid phase second antibody, as well as the use of immune complex precipitation agents and adsorbents, and so forth. Binding reaction systems that can be followed include the so-called competitive binding technique, the sequential saturation technique, the "sandwich" technique, and so forth. Further details concerning the various known heterogeneous systems are readily available in the literature, e.g., German OLS No. 2,618,419, corresponding to U.S. patent application Ser. No. 667,982, filed Mar. 18, 1976 and assigned to the present assignee.

It should be recognized that manipulative techniques involving other orders of addition and other binding reaction formats can be devised for carrying out homogeneous and heterogeneous specific binding assays without departing from the inventive concept embodied herein.

PROSTHETIC GROUP

As previously stated, prosthetic groups are an art recognized distinct class of enzyme cofactors principally characterized by their ability to be regenerated to the active cofactor form by the parent apoenzyme. The present invention employs organic prosthetic groups which can be chemically coupled to the binding component in the labeled conjugate. Usually, the binding constant for association of the apoenzyme and the prosthetic group whose residue is comprised in the labeled conjugate of the present invention is greater than about $10^6$ molar$^{-1}$, and preferably is greater than $10^8$ molar$^{-1}$. The actual binding affinity of the prosthetic group residue appearing in the labeled conjugate may be decreased from that for the free prosthetic group by a few percent or as much as two orders of magnitude without affecting the utility of such prosthetic group residue as a label component in a binding assay.

Following is a table listing several prosthetic groups useful in the present invention, the conjugated enzyme produced by combination with apoenzyme, and binding constants for association of the prosthetic group and the apoenzyme:

| prosthetic group | conjugated enzyme | binding constant (molar-1) | reference |
|---|---|---|---|
| flavine adenine dinucleotide (FAD) | glutathione reductase (human erythrocytes) | $2 \times 10^6$ | 1,3 |
| flavin mononucleotide (FMN) | cytochrome reductase (yeast) | $10^9$ | 2 |
| FMN | NADPH: oxidoreductase ("old yellow enzyme") | $3 \times 10^7$ | 2 |
| FAD | glucose oxidase (*Aspergillus niger*) | $>10^9$ | 4 |
| FAD | lipoamide dehydrogenase | $4 \times 10^6$ | 5 |
| FMN | pyridoxine phosphate oxidase | $5 \times 10^7$ | 6 |
| heme | peroxidase (horse radish) | $>10^9$ | 7 |
| heme | cytochrome C | $>10^9$ | 8 |

[1]Scott et al, J. Biol. Chem. 238:3928(1963).
[2]Haas et al, J. Biol. Chem. 143:341(1942).
[3]Staal et al, Biochim. Biophys. Acta 185:39(1969).
[4]Swoboda, Biochim. Biophys. Acta 175:365(1969).
[5]Visser and Veeger, Biochim. Biophys. Acta 206:224(1970).
[6]Arsenis and McCormick, J. Biol. Chem. 241:330(1966).
[7]Theorell et al, Arkiv. Kemi. Min. O. Geol. 148:1(1940).
[8]Yonetani, J. Biol. Chem. 242:5008(1967).

A preferred prosthetic group/apoenzyme pair is heme and apoperoxidase, and particularly preferred is flavin adenine dinucleotide and apoglucose oxidase. Such prosthetic groups provide ready means for attachment to ligands, ligand analogs and binding partners, and the resulting holoenzymes participate in hydrogen peroxide detection reactions that are well known and utilized analytically and that can be selected to generate colorimetric responses which are advantageous to the clinical laboratory technician.

It should be realized that a particular cofactor may function as a coenzyme or a prosthetic group depending on the enzyme system in which it is placed (e.g., FAD), however, the present invention contemplates the use of such a cofactor only in conjunction with an enzyme system in which it functions as a prosthetic group as defined hereinbefore.

LINKING GROUP

It will be recognized that there are many methods available for linking the binding component of the labeled conjugate, e.g., the ligand to be detected, a binding analog thereof, or a binding partner thereof, to the prosthetic group. The particular chemical character of the linking group will depend upon the nature of the respective available linking sites on the binding component and the prosthetic group. The important considerations in selecting the linking sites usually are (1) preservation of the ability of the linked binding component to participate effectively in the selected binding assay system and (2) preservation of the ability of the linked prosthetic group residue to combine with apoenzyme (or inhibition of such binding ability where such can be relieved upon binding of the labeled conjugate by a binding partner—see illustrative monitoring scheme #1), in both cases, to the extent that a useful assay will result for the particular ligand under assay and for the particular concentrations or amounts in which such ligand is to be detected. Usually the linking group will comprise a chemical bond, usually a single, but sometimes a double bond, or a chain containing between 1 to 14, more commonly 1 to 6, carbon atoms and 0 to 5, more commonly 1 to 3, heteroatoms selected from nitrogen, oxygen, and sulfur.

Both the prosthetic group and the binding component, of course, will offer a great diversity of available functionalities for attachment of the linking group. Commonly the functionalities that can be expected to be available to the linking group are amino, usually primary amino; hydroxyl; halo, usually chloro or bromo; carboxylic acid; aldehyde; keto; isothiocyanate; isocyanate; and so forth. Accordingly, the chemical structure of the linking group itself will vary widely with its terminal groups depending on the functionalities available on the prosthetic group and the binding component and its overall length being a matter of choice within the basic constraints of maintaining the essential prosthetic group and binding component characters of the resulting conjugate. With regard to the length of the linking group in preparing a conjugate for use in a homogeneous assay format, it is usually desirable to use as short a group as possible without causing the resulting binding component in the conjugate to interfer significantly with the prosthetic group activity of the conjugate. Where the binding component is of low molecular weight (e.g., a hapten of molecular weight between 100 and 1000), the linking group is preferably a chemical bond or a 1 to 6 atom chain such as lower alkyl, carbonyl, alkyl carbonyl, amido, alkylamide, and the like. In other circumstances, such as where the binding component in the conjugate is of relatively high molecular weight, such as a polypeptide or protein (e.g., an antibody), a longer linking group is usually desirable to prevent steric hindrance of the apoenzyme combining site of the conjugate. In these cases, the linking group will comprise usually 1 to 14 carbon atoms and 0 to 5 heteroatoms as previously discussed. Chains of any significantly greater length sometimes result in conjugates in which the binding component will tend to fold back into the apoenzyme combining site. With these considerations in mind, examples of linking groups are shown in following Table 1. Particular examples of linking groups will be seen hereinafter and further variations will be readily recognized as being state-of-the-art.

TABLE 1

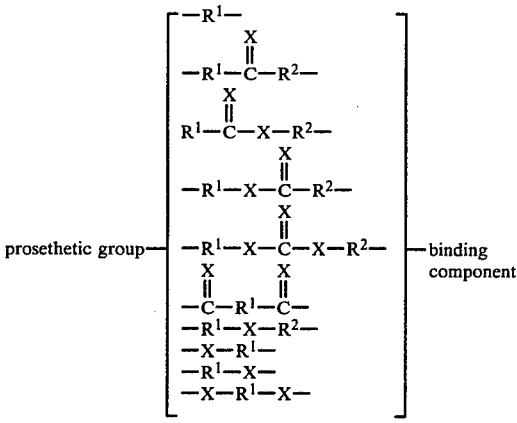

wherein X is imino, sulfur or, preferably, oxygen; and $R^1$ and $R^2$ are, independently, a lower alkylene having 1–6 carbon atoms, such as methylene, ethylene, isopropylene, butylene or hexylene.

APOENZYME

The apoenzyme, or protein portion of the holoenzyme devoid of the prosthetic group, is prepared by splitting the conjugated enzyme and isolating the freed apoenzyme protein. Splitting of the conjugated enzyme can be accomplished in a variety of known manners such as by placing the enzyme in a highly acid solution, e.g., pH less than 2. Likewise, recovery of the apoenzyme can be accomplished by a variety of known techniques, including selective precipitation of the protein or selective adsorption of the low molecular weight freed prosthetic group.

As indicated previously, apoperoxidase and apoglucose oxidase are particularly preferred apoenzymes for use in the present invention because their holoenzymes participate in analytically advantageous hydrogen peroxide reactions. It follows that other related conjugated enzymes, particularly the oxidoreductases, that catalyze reactions producing hydrogen peroxide and that can be split to yield an inactive apoenzyme will find particular application in the present invention. Published methods of isolating apoenzymes are available, particularly for apoglucose oxidase, *Biochim. Biophys. Acta.* 175:365(1969) and for apoperoxidase, *J. Biol. Chem.* 206:109 (1953) and *Arkiv. Kemi. Min O. Geol.* 148:1(1940).

Should there arise the possibility of interference in the assay due to the presence of endogenous prosthetic group in the sample or in any of the reagents or due to prosthetic group contamination of laboratory equipment, glassware or plasticware, such interfering prosthetic group can be readily eliminated by available inactivation techniques. For example, FAD interference can be eliminated by sequential treatment with periodate and ethylene glycol solutions, or by use of other FAD inactivation techniques.

The present invention will now be illustrated, but is not intended to be limited, by the following examples.

EXAMPLE 1

Homogeneous Binding Assays for N-2′,4′-Dinitrophenyl-6-aminocaproate

A. Preparation of the labeled conjugate—$N^6$-(6-aminohexyl)-dinitrophenyl-flavin adenine dinucleotide Flavin $N^6$-aminohexyl-adenine dinucleotide.

$N^6$-Trifluoroacetamidohexyl-adenosine-5′-monophosphate was synthesized by the method of Trayer et al, Biochem. J. 139:609(1974).

Fifty-six milligrams (mg) of $N^6$-trifluoroacetamidohexyl-adenosine-5′-monophosphate (0.1 mmol) was dissolved in about 10 milliliters (ml) of water and 25 microliters ($\mu$l) of tri-n-butylamine (0.1 mmol) was added. The water was removed under vacuum and the residue was dissolved in 10 ml of dry dimethylformamide (DMF) which was then removed under vacuum. The residue was evaporated from dry DMF three more times. The final residue was dissolved in 10 ml of dry DMF. Eighty milligrams of N,N′-carbonyldiimidazole (0.5 mmol) was added and allowed to react for 1.5 hours. Then 15 $\mu$l of water was added and the solvent was removed under vacuum. The residue ($N^6$-trifluoroacetamidohexyl-adenosine-5′-monophosphate imidazolide) was dissolved in 10 ml of DMF.

Forty-seven milligrams of riboflavin-5′-monophosphate (0.1 mmol) was dissolved in about 10 ml of water and added dropwise to 20 ml of acetone containing 43 $\mu$l of tri-n-octylamine (0.1 mmol). A precipitate formed before the addition was complete. The solvent was removed with a rotary evaporator until the riboflavin-5′-monophosphate dissolved. Then 5 ml of acetone and 5–10 ml of DMF were added and the mixture was taken to dryness. The residue was dissolved in 15–20 ml of dry DMF and taken to dryness (this process was repeated three times). The residue was dissolved in 5 ml of DMF and combined with the above-mentioned 10 ml solution of the imidazolide in DMF.

The reaction mixture was allowed to stand at room temperature overnight and then the solvent was removed. The residue was taken up in 50 ml of water and applied to a 2.5×25 centimeter (cm) column of DEAE-cellulose in the bicarbonate form (Whatman DE23, Reeve Angel, Clifton, N.J. U.S.A.). The chromatogram was developed with a linear gradient generated with two liters (1) of water and two liters of 0.3 molar (M) ammonium bicarbonate (23 ml fractions were collected). Thin-layer chromatography on silica gel 60 F254 (E. Merck, Darmstadt, West Germany) using a 7:3 volume:volume (v:v) mixture of ethanol—1 M triethylammonium bicarbonate (pH 7.5) showed that fractions numbered 68 to 73 contained major ($R_f$=0.75) and minor ($R_f$=0.36) yellow compounds. These fractions were pooled and the optical absorption spectrum had maxima at 267, 373 and 450 nanometers (nm).

The solvent was removed from the pooled material and the residue was dissolved in about 5 ml of water. This solution was adjusted to pH 11.0 with 5 N sodium hydroxide and allowed to stand at room temperature for nine hours. Thin-layer chromatography showed that the component with $R_f$=0.75 disappeared while a new yellow material with $R_f$=0.37 appeared. The reaction mixture was adjusted to pH 8.0 with hydrochloric acid and applied to a 2.5×20 cm column of DEAE-cellulose in the bicarbonate form. The chromatogram was developed with a linear gradient developed with one liter of water and one liter of 0.2 M ammonium bicarbonate. The yellow effluent from the column was pooled and the solvent was removed. The residue was adsorbed onto 2 grams (g) of silica gel which was placed atop a 50 g column of silica gel equilibrated with a 9:2 (v:v) mixture of ethanol—1 M triethylammonium bicarbonate (pH 7.5). The column was eluted with an 8:2 (v:v) mixture of ethanol—1 M triethylammonium bicarbonate (pH 7.5), the yellow component with $R_f$=0.37 was collected, and the solvent was removed. The yield based on absorbance at 450 nm was about 10%.

$N^6$-(6-aminohexyl)-dinitrophenyl-flavin adenine dinucleotide.

The residue from above containing flavin $N^6$-aminohexyl-adenine dinucleotide was purified by chromatography on Sephadex G-10 (Pharmacia Fine Chemicals, Uppsala, Sweden). To a 0.9×30 cm column equilibrated with 25 millimolar (mM) sodium bicarbonate (pH 7.5) at room temperature was applied 1 ml of an approximately 10 mM solution of the $N^6$-FAD derivative in water. The first eluted peak of material absorbing at 450 nm was collected and rechromatographed on Sephadex G-10 and the first eluting peak collected again.

0.5 ml (0.63 μmol) of the purified $N^6$-FAD derivative in 25 mM sodium bicarbonate (pH 7.5) was mixed with 2 ml of ethanol and 10 μl of $^3$-H-dinitrofluorobenzene (6.3 μmol, 50 μCi) in ethanol were added (the tritiated dinitrofluorobenzene was obtained from the Radiochemical Centre, Amersham UK). The reaction mixture was shaken continuously overnight in the dark at room temperature and then applied to a 0.9×30 cm column of Sephadex G-10 equilibrated with 0.1 M phosphate buffer (pH 7.0) containing 0.1% sodium azide. The single peak of material absorbing at 450 nm was collected and found to contain 8% of the radioactive label.

B. Preparation of apoglucose oxidase

Purified glucose oxidase with low catalase activity obtained from the Research Products Division of Miles Laboratories, Inc., Elkhart, Ind. U.S.A. was dialyzed twice for 12 hours each against 0.5% weight:volume (w:v) mannitol (30 volumes each). Aliquots of the dialyzate containing 100 milligrams (mg) of glucose oxidase each were lyophilized and stored at −20° C.

Bovine serum albumin (200 mg) was dissolved in 12 ml of water adjusted to pH 1.6 with concentrated sulfuric acid, mixed with 150 mg charcoal (RIA grade from Schwarz-Mann, Orangeburg, N.Y. U.S.A.), and cooled to 0° C. Lyophilized glucose oxidase (100 mg) was redissolved in 3.1 ml of water and 3 ml was added to the stirred albumin-charcoal suspension with continued stirring for 3 minutes. The suspension was then filtered through a 0.8 micron, 25 millimeter (mm) diameter Millipore filter (Millipore Corp., Bedford, Mass. U.S.A.) mounted in a Sweenex filter apparatus (Millipore Corp.) on a 50 ml disposable plastic syringe. The filtrate was quickly neutralized to pH 7.0 by addition of 2 ml of 0.4 M phosphate buffer (pH 7.6) and thereafter 5 N sodium hydroxide. Dry charcoal (150 mg) was then added and stirred for one hour at 0° C. The resulting suspension was filtered first through a 0.8 micron Millipore filter and then through a 0.22 micron Millipore filter. To the filtrate was added glycerol to 25% (v:v) and the stabilized apoglucose oxidase preparation was stored at 4° C.

C. Assay Reagents

1. Labeled conjugate—$N^6$-(6-aminohexyl)-DNP-FAD was diluted in 0.05 M phosphate buffer (pH 7.0) to a concentration of 118 nM.

2. Apoenzyme—Apoglucose oxidase was diluted with 0.1 M phosphate buffer (pH 7.0) containing 0.1% bovine serum albumin to a concentration of 958 nM FAD binding sites. The FAD binding site concentration of the apoenzyme preparation was determined experimentally by measuring the minimum amount of FAD required to give maximum glucose oxidase activity when incubated with the apoenzyme.

3. Antiserum—Antiserum against a dinitrophenyl-bovine serum albumin conjugate was obtained from Miles-Yeda, Ltd., Rehevot, Israel and was diluted 31 fold in 0.1 M phosphate buffer (pH 7.0) containing 0.1% bovine serum albumin.

4. Standards—The standard solutions contained known concentrations of N-2′,4′-dinitrophenyl-6-aminocaproate prepared in 0.05 M phosphate buffer (pH 7.0).

5. Monitoring reagent—A glucose oxidase reagent was prepared by mixing 45 ml of 0.1 M phosphate buffer (pH 7.0) containing 15 mM ethylenediamine tetraacetic acid, 9 ml of 11.5 mM 3,5-dichloro-2-hydroxybenzene sulfonate in water adjusted to pH 7 with sodium hydroxide, 9 ml of 11.5 mM 4-aminoantipyrine in water containing 1.25 mg/ml of peroxidase (Miles Laboratories, Inc., Elkhart, Ind. U.S.A.), and 6 ml of 1.0 M glucose in aqueous saturated benzoic acid solution.

D. Assay Procedures

Addition of apoenzyme before initiation of binding reaction

Method #1—The following were added in sequence to separate reaction cuvettes: 0.1 ml of the labeled conjugate solution, 0.05 ml of a selected standard solution, 0.1 ml of the antiserum solution, 2.0 ml of the monitoring reagent, and 0.1 ml of the apoenzyme solution. Each reaction mixture was incubated for 30 minutes at 30° C. and the absorbance at 520 nm measured.

Method #2—The following were added in sequence to separate reaction cuvettes: 0.1 ml of the labeled conjugate solution, 0.05 ml of a selected standard solution, 0.1 ml of the antiserum solution, and 0.1 ml of the apoenzyme solution. Each reaction mixture was incubated for 20 minutes at room temperature and then 2.0 ml of the monitoring reagent was added to each. After further incubation for 15 minutes at 30° C. the absorbance at 520 nm was measured in each cuvette.

Addition of apoenzyme after initiation of binding reaction

Method #3—The following were added in sequence to separate reaction cuvettes: 0.1 ml of labeled conjugate solution, 0.05 ml of a selected standard solution, and 0.1 ml of the antiserum solution. Each reaction mixture was incubated for 20 minutes at room temperature and then 2.0 ml of the monitoring reagent and 0.1 ml of the apoenzyme solution were added to each. After further incubation for 30 minutes at 30° C. the absorbance at 520 nm was measured in each cuvette.

Method #4—The following were added in sequence to separate reaction cuvettes: 0.1 ml of the labeled conjugate solution, 0.05 ml of a selected standard solution, and 0.1 ml of the antiserum solution. Each reaction mixture was incubated for 20 minutes at room temperature and then 0.1 ml of the apoenzyme solution was added to each. After further incubation for 20 minutes 2.0 ml of the monitoring reagent was added to each cuvette. Then each reaction mixture was incubated for 15 minutes at 30° C. and the absorbance at 520 nm was measured in each cuvette.

E. Results

Following is Table 2 showing the results of the four assay procedures in measuring N-2′,4′-dinitrophenyl-6-aminocaproate. The concentrations of N-2′,4′-dinitrophenyl-6-aminocaproate are expressed as concentrations in the final 2.35 ml reaction mixture volumes. The absorbance results are expressed as the average of duplicate runs corrected for residual enzyme activity and background absorbance in the reagents. The correction factor is given for each assay method at the end of Table 2 and was determined by experimental runs substituting 0.1 M phosphate buffer (pH 7.0) for all of the labeled conjugate, standard, and anti-serum solutions.

TABLE 2

| Concentration of N—2′,4′-dinitrophenyl-6-aminoca- | Corrected Average Absorbance at 520 nm | | | |
|---|---|---|---|---|
| proate (nM) | Method #1 | Method #2 | Method #3 | Method #4 |
| 1021 | 0.274 | 1.089 | 0.205 | 1.399 |
| 511 | 0.263 | 0.992 | 0.197 | 1.302 |

TABLE 2-continued

| Concentration of N—2',4'-dinitrophenyl-6-aminocaproate (nM) | Corrected Average Absorbance at 520 nm | | | |
|---|---|---|---|---|
| | Method #1 | Method #2 | Method #3 | Method #4 |
| 255 | 0.235 | 0.898 | 0.187 | 1.136 |
| 128 | 0.221 | 0.689 | 0.173 | 0.958 |
| 64 | 0.194 | 0.545 | 0.155 | 0.737 |
| 32 | 0.165 | 0.365 | 0.134 | 0.534 |
| 16 | 0.141 | 0.276 | 0.133 | 0.353 |
| 8 | 0.134 | 0.225 | 0.122 | 0.257 |
| 4 | 0.122 | 0.193 | 0.104 | 0.229 |
| 2 | 0.123 | 0.187 | 0.109 | 0.215 |
| 0 | 0.107 | 0.171 | 0.101 | 0.199 |
| correction factor | 0.241 | 0.108 | 0.216 | 0.108 |

The results demonstrate that the present invention provides a specific binding assay method of the homogeneous type wherein apoenzyme is introduced either before or after initiation of the binding reaction.

EXAMPLE 2

Heterogeneous Binding Assay for Thyroxine

A. Preparation of the labeled conjugate-$N^6$-(2-aminoethyl)thyroxine-flavin adenine dinucleotide 6-(2-Aminoethyl)-amino-9-(2',3'-O-isopropylidine-$\beta$-D-ribofuranosyl) purine.

13.56 g (41.5 mmol) of 6-chloro-9-(2',3'-O-isopropylidene-$\beta$-D-ribofuranosyl) purine [Hampton et al, J. Am. Chem. Soc. 83: 150(1961)] was added with stirring over a 15 minute period to a cold excess of 1,2-diaminoethane (75 ml). The resulting solution was allowed to stand at room temperature for 24 hours. The solution was evaporated in vacuo and the resulting yellow oil was stirred with 50 ml of cold, saturated sodium bicarbonate. The mixture was evaporated in vacuo and the resulting residue was further repeatedly evaporated in vacuo first from water (3 times from 50 ml) and then from 2-propanol (4 times from 50 ml) to obtain a yellow glass (15 g). A portion (3 g) of the glass was passed through a 25×55 centimeter (cm) Dowex 50W-X2 cation exchange column in the ammonium form (Bio-Rad Laboratories, Richmond, Calif. USA).

The column was eluted with a linear gradient generated with 2 l of water and 2 l of 0.5 M ammonium bicarbonate. The elution was completed using a linear gradient generated with 2 l each of 0.5 M and 1 M ammonium bicarbonate. The effluent from the column was collected in 19 ml fractions and monitored by elution on silica gel thin layer chromatography (TLC) plates (E. Merck, Darmstadt, West Germany) with a 9:1 (v:v) mixture of ethanol and ammonium hydroxide. The developed TLC plates were examined under ultraviolet light, then sprayed with ninhydrin reagent [Randerath, Thin Layer Chromatography, Academic Press (1966)]. Fractions numbered 250 through 350 from the column chromatography were combined and evaporated in vacuo leaving the desired purine as a pale yellow amorphous glass (1.5 g).

Analysis: Calculated for $C_{15}H_{22}N_6O_4$: C, 51.42; H, 6.33; N, 23.99. Found: C, 50.92; H, 6.54; N, 23.01. NMR (60 MHz, CDCl$_3$): $\delta$1.37 (s,3H, isopropylidene), 1.63 (s,3H, isopropylidene), 5.92 (d, 1H, 1'-ribose), 7.90 (s, 1H, purine), 8.26 (s, 1H, purine). Optical Rotation $[\alpha]_D^{20} = -74.85°$ (c 1.0, CH$_3$OH).

The remaining crude product (12 g) was purified by chromatography on Dowex 50W-X2 as described above. The overall yield was 8 g (55%).

$\alpha$-(N-Trifluoroacetyl)-amino-$\beta$-[3,5-diiodo-4-(3',5'-diiodo-4'-hydroxyphenoxy)-phenyl] propanoic acid.

This compound was prepared by the method of Blank, J. Pharm. Sci. 53:1333(1964). To a cooled (0° C.), stirred suspension of 5 g (6.4 mmol) of L-thyroxine (Sigma Chemical Co., St. Louis, Mo. USA) in 60 ml of dry ethyl acetate was added 11.5 ml of trifluoroacetic acid and 1.9 ml of trifluoroacetic anhydride. After 30 minutes the resulting clear solution was washed three times with 30 ml of water, once with 30 ml of 5% sodium bicarbonate, and twice with 50 ml of saturated sodium chloride. The combined aqueous washings were extracted twice with 20 ml of ethyl acetate. The ethyl acetate layers were combined and washed with 30 ml of water, then dried over magnesium sulfate. The dried ethyl acetate solution was evaporated in vacuo leaving a white solid. Recrystallization from a mixture of ethyl ether and petroleum ether gave a pinkish-white solid (3.95 g, 70.5% yield) melting at 228°-230° C. with decomposition.

Analysis: Calculated for $C_{17}H_{10}F_3I_4NO_5$: C, 23.39; H, 1.15; N, 1.60. Found: C, 23.00; H, 1.05; N, 1.65. NMR [60 MHz, DCON(CD$_3$)$_2$] $\delta$7.28 (s, 2H, aromatic), 8.03 (s, 2H, aromatic), 9.7 (m, 1H, amido). IR (KCl): 1700 (>C=O). Optical Rotation $[\alpha]_D^{25} = -14.97°$ (c 1.0, dimethylsulfoxide).

A second recrystallization produced a second precipitate (0.95 g) m.p. 224°-228° C. with decomposition. The overall yield was 87.5%.

N-{2-[N-(Trifluoroacetyl)-3,3',5,5'-tetraiodothyronyl]aminoethyl}-2',3'-O-isopropylidene adenosine.

A solution of 8.72 g (10.0 mmol) of $\alpha$-(N-trifluoroacetyl)amino-$\beta$-[3,5-diiodo-4-(3',5'-diiodo-4'-hydroxyphenoxy)-phenyl]propanoic acid and 3.86 g (11.0 mmol) of 6-(2-aminoethyl)amino-9-(2',3'-O-isopropylidene-$\beta$-D-ribofuranosyl) purine in 50 ml of dry dimethylacetamide was prepared under a dry argon atmosphere at −20° C. To this cold stirred solution was added a solution of 3.04 g (11.0 mmol) of diphenylphosphoryl azide (Aldrich Chemical Co., Milwaukee, Wis. USA) in 10 ml of dry dimethylacetamide followed by the addition of 1.6 ml (11.0 mmol) of dry triethylamine. The solution was left at room temperature for 22 hours. The solution was then added dropwise to 300 ml of cold (0° C.) water with stirring. The resulting white precipitate was collected by filtration and dried in vacuo (56° C.) to give 13.0 g of a light cream colored solid. The solid was dissolved in 500 ml of acetone and the solution was concentrated by boiling. The white solid which precipitated from the boiling acetone solution was collected by filtration while hot. Continued boiling of the filtrate produced two additional precipitates. The three precipitates were combined to give 8 g (66.6% yield) of a white solid, m.p. 198°-200° C. (decomposed).

Analysis: Calculated for $C_{32}H_{30}F_3I_4N_7O_8$: C, 31.89; H, 2.51; N, 8.14. Found: C, 31.95; H, 2.60; N, 7.86. NMR [220 MHz, (CD$_3$)$_2$SO] $\delta$1.32 (s, 3H, isopropylidene), 1.55 (s, 3H, isopropylidene), 6.14 (d, 1H, 1'-ribose), 7.02 (s, 2H, thyroxine), 7.82 (s, 2H, thyroxine), 8.25 (s, 1H, purine), 8.36 (s, 1H, purine), 8.41 (t, 1H, J=6, amido), 9.64 (d, 1H, J=8, trifluoroacetamido). Optical Rotation $[\alpha]_D^{25} = -11.82°$ (c 1.0, pyridine).

N-{2-[N-(Trifluoroacetyl)-3,3',5,5'-tetraiodothyronyl]aminoethyl}-2',3'-O-isopropylidene-5'-adenylic acid monotriethylamine salt monohydrate.

A solution of 1.2 g (1.0 mmol) of N-{2-[N-(trifluoroacetyl)-3,3',5,5'-tetraiodothyronyl]-aminoethyl}-2',3'-O-isopropylidene adenosine in 10 ml of dry triethylphosphate was prepared under a dry argon atmosphere at 0° C. To the cold, stirred solution was added 0.45 ml (5 mmol) of phosphorous oxychloride. The resulting solution was kept for 24 hours at 0° C., then added dropwise with stirring to 1 l of ice water. The resulting precipitate was collected by filtration and dried in vacuo to give 1.23 g of a white solid. The solid was dissolved in acetone and 0.32 ml (2.2 mmol) of triethylamine was added. A precipitate formed. The mixture was evaporated in vacuo and the resulting residue lixiviated with dry acetone, then recrystalized from a mixture of dry methyl alcohol and dry ethyl ether to give 390 mg (27.8% yield) of a white solid, m.p. 173°–183° C. (decomposed).

Analysis: Calculated for $C_{38}H_{48}F_3I_4N_8O_{12}P$: C, 32.50; H, 3.45; N, 7.98. Found: C, 32.24; H, 3.08; N, 7.58. NMR [60 MHz, $(CD_3)_2SO$] $\delta 1.53$ (s, 3H, isopropylidene), 6.2 (d, 1H, 1'H-ribose), 7.1 (s, 2H, thyroxine aromatic), 7.87 (s, 2H, thyroxine aromatic), 8.27 (s, 1H, purine), 8.52 (s, 1H, purine). Optical Rotation $[\alpha]_D^{25} = -17.50°$ (c 1.0, $CH_3OH$).

N-{2-[N-(Trifluoroacetyl)-3,3',5,5'-tetraiodothyronyl]aminoethyl}-5'-adenylic acid.

200 mg (0.14 mmol) of N-{2-[N-(trifluoroacetyl)-3,3',5,5'-tetraiodothyronyl]-aminoethyl}-2',3'-O-isopropylidene-5'-adenylic acid monotriethylamine salt monohydrate was suspended in 1 ml of water (0° C.) and trifluoroacetic acid (9 ml) was added dropwise with stirring. After 30 minutes a clear solution was obtained. The solution was kept cold (0° C.) for an additional 15 hours, then evaporated in vacuo (30° C.). The resulting residue was evaporated four times in vacuo (25° C.) from 20 ml volumes of anhydrous ethyl alcohol and then dried in vacuo (25° C.) leaving a white solid.

The solid was stirred for 30 minutes with 10 ml of cold methyl alcohol, then collected by filtration and dried in vacuo (25° C.) to give a white solid (135 mg, 76% yield) which slowly melted with decomposition above 188° C.

Analysis: Calculated for $C_{29}H_{27}F_3I_4N_7O_{11}P$: C, 27.97; H, 2.19; N, 7.87. Found: C, 28.11; H, 2.31; N, 7.65. NMR [220 MHz, $(CD_3)_2SO$] $\delta 5.95$ (d, 1H, 1'-ribose), 7.04 (s, 2H, thyroxine aromatic), 7.84 (s, 2H, thyroxine aromatic), 8.25 (s, 1H, purine), 8.36 (s, 1H, purine), 8.43 (m, 1H, amido), 9.66 (d, 1H, trifluoroacetamido) Optical Rotation $[\alpha]_D^{25} = -2.72°$ (c 1.0, pyridine).

Flavin adenine dinucleotide-thyroxine conjugate.

498 mg (0.4 mmol) of N-{2-[N-(trifluoroacetyl)-3,3',5,5'-tetraiodothyronyl]-aminoethyl}-5'-adenylic acid was dissolved in 10 ml of dry dimethylformamide and tri-n-butylamine (96 μl, 0.4 mmol) was added followed by the addition of 1,1'-carbonyldiimidazole (320 mg, 2.0 mmol). After stirring for 18 hours at room temperature in the absence of moisture, water (280 μl) was added and then the solvent evaporated in vacuo.

The resulting oil was dried by repeated in vacuo evaporation from dry dimethylforamide (4 times from 10 ml). The resulting phosphorimidazolidate was redissolved in 10 ml of dry dimethylforamide and added dropwise to a 0.4 mmol solution of the tri-n-octylamine salt of riboflavin-5'-monophosphate in 10 ml of dry dimethylformamide. The salt was prepared by adding a solution of the ammonium salt of riboflavin-5'-monophosphate (192 mg, 0.4 mmol) in 10 ml of water to a stirred solution of tri-n-octylamine (176 μl, 0.4 mmol) in 100 ml of acetone. After 30 minutes, the resulting mixture was evaporated in vacuo. The residue was dried by repeated evaporation in vacuo from dry dimethylformamide leaving the salt as an orange solid.

The above solution containing the phosphorimidazolidate and the riboflavin-5'-monophosphate salt was divided into two equal aliquots after 24 hours and one aliquot was evaporated in vacuo. The resulting residue was chromatographed on a column (2.5×78 cm) prepared from 100 g of Sephadex LH-20 (Pharmacia Fine Chemicals, Uppsala, Sweden) which had been preswollen (18 hours) in a 19:1 (v:v) mixture of dimethylformamide and triethylammonium bicarbonate (1 M, pH 7.5). The column was eluted with the above 19:1 (v:v) mixture and 10 ml fractions were collected. The effluent from the column was monitored by elution on silica gel 60 silanised RP-2 TLC plates (E. Merck, Darmstadt, West Germany).

The TLC plates were developed using a 40:40:25:1:1 (v:v) mixture of acetone, chloroform, methyl alcohol, water, and triethylamine. Fractions numbered 11 through 17 from the abovementioned column chromatography were combined and evaporated in vacuo. The residue was chromatographed on a column (2.5×75 cm) prepared from 125 g of Sephadex LH-20 which had been preswollen (18 hours) in 0.3 M ammonium bicarbonate. The column was eluted with 0.3 M ammonium bicarbonate collecting 10 ml fractions. The effluent was monitored by absorption of ultraviolet light at 254 nm. The volume of the fractions was increased to 20 ml beginning with fraction number 150. The salt concentration of the eluent was decreased in a stepwise fashion as follows: 0.15 M ammonium bicarbonate at fraction number 295, 0.075 M ammonium bicarbonate at fraction number 376, and water at fraction number 430. A total of 480 fractions was collected. Fractions numbered 200 through 235 were combined and evaporated in vacuo leaving the labeled conjugate as a yellow-orange residue. An alkaline, aqueous solution of this residue exhibited ultraviolet absorption maxima at the following wavelengths: 266 nm, 350 nm, 373 nm, and 450 nm. The yield, estimated from the absorption at 450, was about 5%.

A phosphodiesterase preparation (Worthington Biochemical Corp., Freehold, N.J. USA) isolated from snake venom (*Crotalus Adamanteus*) hydrolyzed the above product to riboflavin-5'-monophosphate and the thyroxine substituted 5'-adenylic acid wherein the trifluoroacetyl blocking group had been removed.

Further description of the preparation of labeled conjugates of this type may be found in U.S. Pat. No. 4,171,432 assigned to the present assignee.

B. Preparation of apoglucose oxidase

Apoenzyme prepared according to part B of Example 1 was used.

C. Assay Reagents

1. Labeled conjugate—$N^6$-(2-aminoethyl)-thyroxine-FAD was diluted in 0.1 M phosphate buffer (pH 7) to a concentration of 1 μM.

2. Apoenzyme—Apoglucose oxidase was diluted with 0.1 M phosphate buffer (pH 7) to a concentration of 0.6 μM FAD binding sites (defined as in part C-2 of Example 1).

3. Insolubilized antibody—A washed, moist cake of Sepharose 4B gel (Pharmacia Fine Chemicals, Uppsala, Sweden) activated by cyanogen bromide according to the method of March et al, *Anal. Biochem.* 60:119 (1974) was added to a solution of 85 mg of antibody (isolated from antiserum against a thyroxine-bovine serum albumin conjugate) in 20 ml of 0.1 M phosphate buffer (pH 7.0) and agitated slowly for 36 hours at 4° C. Upon completion of the coupling reaction, 1 ml of 1 M alanine was added and shaking continued for 4 more hours to block unreacted sites. The resulting Sepharose-bound antibody was washed on a scintered funnel with 400 ml each of 50 mM sodium acetate—500 mM sodium chloride (pH 5), and 50 mM phosphate buffer—500 mM sodium chloride (pH 7), and 800 ml of 100 mM phosphate buffer (pH 7). The moist filter cake was then suspended in 100 mM phosphate buffer (pH 7) containing 0.01% sodium azide to give 22 ml of an about 50% suspension.

4. Standard—A 1.15 mM stock solution of thyroxine in 5 mM sodium hydroxide was diluted to 2 μM in 0.1 M phosphate buffer (pH 7).

5. Monitoring reagent—A glucose oxidase assay reagent was prepared to contain the following mixture per 130 μl: 25 μl of 1.2 mg/ml peroxidase (Sigma Chemical Co., St. Louis, Mo. USA) in 0.1 M phosphate buffer (pH 7), 5 μl of 10 mM 4-aminoantipyrine in water, 20 μl of 25 mM 3,5-dichloro-2-hydroxybenzene sulfonate in 0.1 M phosphate buffer (pH 7), 30 μl of 16.5% bovine serum albumin in 0.1 M phosphate buffer (pH 7), and 50 μl of 1 M glucose in aqueous saturated benzoic acid solution.

D. Assay Procedure

Binding reaction mixtures were prepared by mixing 150 μl of the insolubilized antibody suspension, 80 μl of the labeled conjugate solution, various amounts of the standard thyroxine solution to give varying concentrations of thyroxine in the reaction mixtures, and a sufficient volume of 0.1 M phosphate buffer (pH 7) to make a total volume of 500 μl. The reaction mixtures were incubated with shaking for two hours at 25° C. Each reaction mixture was then vacuum filtered through a glass wool plugged, dry pasteur pipette previously treated with periodate and ethylene glycol solutions to eliminate possible FAD contamination. To a 300 μl aliquot of each filtrate was added 130 μl of the monitoring reagent and 50 μl of the apoenzyme solution. After one hour, the absorbance of each reaction mixture was measured at 520 nm.

E. Results

Following is Table 3 showing the results of the assay procedure in measuring thyroxine. The absorbance results are expressed as the average of duplicate runs corrected for residual enzyme activity in the apoenzyme solution (absorbance of 0.522) and for endogenous FAD in the antibody suspension (absorbance 0.142).

TABLE 3

| Volume of Thyroxine Standard Added (μl) | Corrected Average Absorbance at 520 nm |
|---|---|
| 0 | 0.223 |
| 25 | 0.221 |
| 75 | 0.281 |
| 250 | 0.286 |

The results demonstrate that the present invention provides a useful specific binding assay method of the heterogeneous type.

What is claimed is:

1. An enzyme-labeled compound having the formula:

Apo-Pr-R-L wherein Pr represents an organic prosthetic group, Apo is an apoenzyme combined with said prosthetic group forming its conjugated enzyme, R is a linking group, and L is a hapten of molecular weight between 100 and 1000; wherein said hapten and said prosthetic group are coupled through said linking group at a site on the hapten away from its specific binding site and at a site on the prosthetic group away from its active binding site for the apoenzyme.

2. The labeled compound of claim 1 wherein said conjugated enzyme is catalytically active.

3. The labeled compound of claim 1 wherein the binding constant for association of said apoenzyme and said prosthetic group is greater than about $10^6$ molar$^{-1}$.

4. The labeled compound of claim 1 wherein said prosthetic group is flavin adenine dinucleotide, flavin mononucleotide or heme.

5. The labeled compound of claim 1 wherein said prosthetic group is flavin adenine dinucleotide or heme, and said apoenzyme is apoglucose oxidase or apoperoxidase, respectively.

6. The labeled compound of claim 1 wherein said linking group is a chain containing 1 to 14 carbon atoms and 0 to 5 heteroatoms selected from nitrogen, oxygen and sulfur.

7. The labeled compound of claim 1 wherein said hapten is an iodothyronine thyroid hormone.

8. The labeled compound of claim 7 wherein said thyroid hormone is thyroxine.

9. The labeled compound of any one of claims 7 and 8, wherein said prosthetic group is flavin adenine dinucleotide and said apoenzyme is apoglucose oxidase.

10. A method of preparing an enzyme-labeled antigen or hapten for use in specific binding assays for determining said antigen or hapten or a specific binding partner thereof, comprising the steps of:
  covalently coupling said antigen or hapten, at a site thereon away from its specific binding locus, to an organic prosthetic group, at a site thereon away from its active binding locus for an apoenzyme, and
  combining the resulting coupled product with said apoenzyme to form a conjugated enzyme with said prosthetic group in said coupled product yielding an enzyme-labeled antigen or hapten.

11. The method of claim 10 wherein the binding constant for association of said apoenzyme and said prosthetic group is greater than about $10^6$ molar$^{-1}$.

12. The method of claim 10 wherein said conjugated enzyme in the resulting enzyme-labeled antigen or hapten is catalytically active.

13. The method of claim 10 wherein said prosthetic group is flavin adenine dinucleotide, flavin mononucleotide, or heme.

14. The method of claim 10 wherein said prosthetic group is flavin adenine dinucleotide or heme, and said apoenzyme is apoglucose oxidase or apoperoxidase, respectively.

15. The method of any one of claims 10 and 11–14 wherein said antigen or hapten is a hapten of molecular weight between 100 and 1000.

16. The method of claim 10 wherein said prosthetic group is flavin adenine dinucleotide.

17. The method of claim 16 wherein said apoenzyme is apoglucose oxidase.

18. The method of claim 17 wherein said antigen or hapten is an iodothyronine thyroid hormone.

19. The method of claim 18 wherein flavin adenine dinucleotide is covalently coupled to said iodothyronine hormone through a linking group between the $N^6$-amino group in the adenine nucleus of the former and the carboxyl group of the latter.

20. The method of claim 19 wherein said linking group is a chain containing 1 to 14 carbon atoms and 0 to 5 heteroatoms selected from nitrogen, oxygen and sulfur.

21. The method of claim 20 wherein said iodothyronine hormone is thyroxine.

* * * * *